United States Patent [19]

Gravener

[11] Patent Number: 5,441,193
[45] Date of Patent: Aug. 15, 1995

[54] SURGICAL FASTENER APPLYING APPARATUS WITH RESILIENT FILM

[75] Inventor: Roy D. Gravener, Fairfield, Conn.

[73] Assignee: United States Surgical Corporation, Norwalk, Conn.

[21] Appl. No.: 125,906

[22] Filed: Sep. 23, 1993

[51] Int. Cl.$^6$ .......................................... A61B 17/068
[52] U.S. Cl. .................................. 227/176; 227/175; 227/19; 606/151
[58] Field of Search ............... 227/175, 176, 177, 179, 227/180, 19; 606/151, 213, 215, 219, 220, 221

[56] References Cited

U.S. PATENT DOCUMENTS

| | | |
|---|---|---|
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 4,242,902 | 1/1981 | Green . |
| 4,299,224 | 11/1981 | Noiles . |
| 4,354,628 | 10/1982 | Green . |
| 4,383,634 | 5/1983 | Green . |
| 4,412,539 | 11/1983 | Jarvik . |
| 4,508,253 | 4/1985 | Green . |
| 4,520,817 | 6/1985 | Green . |
| 4,522,327 | 6/1985 | Korthoff et al. . |
| 4,568,009 | 2/1986 | Green . |
| 4,573,622 | 3/1986 | Green et al. . |
| 4,616,650 | 10/1986 | Green et al. . |
| 4,624,254 | 11/1986 | McGarry et al. . |
| 4,665,916 | 5/1987 | Green . |
| 4,728,020 | 3/1988 | Green et al. . |
| 4,881,544 | 11/1989 | Green et al. . |
| 4,881,545 | 11/1989 | Isaacs et al. . |
| 4,932,960 | 6/1990 | Green et al. . |
| 4,955,959 | 9/1990 | Tompkins . |
| 5,014,899 | 5/1991 | Presty et al. . |
| 5,040,715 | 8/1991 | Green et al. . |
| 5,084,057 | 1/1992 | Green et al. . |
| 5,100,042 | 3/1992 | Gravener et al. . |
| 5,100,420 | 3/1992 | Green et al. . |
| 5,116,349 | 5/1992 | Aranyi . |
| 5,133,738 | 7/1992 | Korthoff et al. . |
| 5,156,614 | 10/1992 | Green et al. . |
| 5,236,629 | 11/1993 | Trumbull et al. . |

Primary Examiner—Scott A. Smith

[57] ABSTRACT

A surgical device for clamping body tissue between two movable members, for example a surgical stapling apparatus, includes a sheet of curved resilient material attached to one or both of the members for biasing the body tissue when the members are closed onto the tissue.

24 Claims, 2 Drawing Sheets

SURGICAL FASTENER APPLYING APPARATUS WITH RESILIENT FILM

BACKGROUND OF THE INVENTION

1. Field of the Invention

The present invention relates to a resilient film biasing means which may be incorporated with surgical fastener applying apparatus or surgical fasteners.

2. Background of the Art

Various types of surgical fasteners and fastener applying apparatus are known in the art.

Surgical fasteners comprise unitary staples such as metal staples which are closed by crimping the legs; two-part fasteners, usually made of bioabsorbable polymer, which are closed by joining the interlocking fastener portion and retainer portion such as shown in U.S. Pat. No. 4,932,960; and U-shaped or V-shaped surgical clips which are applied by bending the legs toward each other.

For example, U.S. Pat. Nos. 5,116,349; 4,881,544; 4,881,545; 5,100,042; 4,508,253; 4,522,327; 4,568,009; 4,573,622; 4,665,916; 4,728,020; 4,354,628; 4,383,634; and 3,494,533, all of which are herein incorporated by reference, describe apparatus for simultaneously applying a plurality of metal staple type fasteners or two-part bioabsorbable fasteners.

Apparatus for sequentially applying metal staples or two-part polymeric fasteners are described, for example, in U.S. Pat. Nos. 5,156,614; 4,955,959; 5,014,899; 4,520,817; 3,499,591; 3,490,675; and 3,079,606, all of which are herein incorporated by reference.

Clip applying apparatus are described in U.S. Pat. Nos. 4,616,650; 4,624,254; 4,299,224; 4,412,539; and 4,242,902, all of which are herein incorporated by reference.

Fastener applying apparatus may be adapted for endoscopic/laparoscopic use, as exemplified in U.S. Pat. Nos. 5,040,715; 5,084,057; and 5,100,420, all of which are herein incorporated by reference.

One problem associated with surgical operations is poor hemostasis, i.e. oozing of blood or other body fluid at the site of the operation during healing. Typically, oozing is controlled by optimizing the gap between the cartridge and anvil, the spacing between fasteners, and the size of the fasteners. In other words, the appropriate size instrument must be chosen for a particular application. However, it would be advantageous to maintain satisfactory hemostasis over a wider range of gap spacing and fastener size so that any particular size of 1506X instrument would be suitable for a wider variety of surgical applications.

Another problem is the formation of surgical adhesions, which are the undesirable joining of body tissue during the healing after a surgical procedure.

What is needed is a convenient way to overcome these problems.

SUMMARY OF THE INVENTION

A surgical device is provided herein which comprises first and second elongated members movable between an open first position wherein the members are relatively spaced apart from each other and a closed second position wherein the members are relatively close to each other for clamping body tissue therebetween, the members having mutually facing surfaces; and at least one sheet of resilient material attached to and covering at least a portion of the mutually facing surface of at least one of the members, the sheet of resilient material having an inwardly directed convexly curved surface. The surgical device can comprise a surgical clip wherein the first and second elongated members comprise clip legs. The surgical clip can be fabricated from stainless steel, titanium, or bioabsorbable synthetic polymer such as polymers of glycolide, lactide, caprolactone, p-dioxanone, or trimethylene carbonate, and physical and chemical combinations thereof. A polymeric clip can be integrally fabricated with the resilient sheet.

The first and second members can also be the cartridge and anvil, respectively, of a surgical fastener applying apparatus. More particularly, an apparatus for applying surgical fasteners to body tissue is provided herein. The apparatus comprises: a cartridge for holding a plurality of surgical fasteners; an anvil having means for closure of surgical fasteners; means for moving the cartridge and the anvil between an open first position wherein the cartridge and the anvil are relatively spaced apart from each other and a closed second position wherein the cartridge and the anvil are relatively close to each other for clamping body tissue therebetween; means for driving the fasteners from the cartridge into the anvil for closure thereof; and a sheet of resilient material positioned between the cartridge and the anvil so that substantially all of the fasteners pass at least partially through the sheet of resilient material in response to firing of the apparatus.

The fasteners have two legs extending from a backspan and the legs penetrate the resilient sheet when the apparatus is fired. The fasteners can be metallic or polymeric staples, or two-part fasteners each including a fastener portion having two legs parallely extending from a backspan, and a retainer portion. The fasteners can be arranged in parallel rows oriented transverse to a longitudinal axis of the apparatus as, for example, in an apparatus wherein substantially all of the fasteners are fired simultaneously. Or the fasteners can be arranged in rows oriented parallel to a longitudinal axis of the apparatus as, for example, in an apparatus wherein the fasteners are sequentially fired.

The resilient sheet can be mounted to the cartridge or the anvil by means of adhesive and/or a projection and slot engagement. Optionally, the resilient sheet includes perforations for permitting separation of at least a portion of the sheet and may also include apertures for permitting free passage therethrough of the staple legs without significantly increasing the penetration force.

The resilient sheet may be fabricated from bioabsorbable synthetic polymer and may include therapeutic components combined therewith.

Advantageously, the resilient film of the present invention permits the use of less expensive and narrower instruments with fewer rows of staples. More even clamping pressure is achieved.

DETAILED DESCRIPTION OF PREFERRED EMBODIMENT(S)

The present invention employs a resilient film, or sheet, on the surgical fastener applying apparatus to distribute the force of the fastener application. Nonuniformities of clamping pressure are thereby more evenly distributed. As used herein the term fastener refers to staple type fasteners which close by crimping the legs, two-part polymeric fasteners of bioabsorbable material (e.g. polyglycolide/polylactide homopolymers or copolymers) or surgical clips (e.g. U-shaped, V-shaped). Although any of these types of fasteners may be used, the present invention will be described herein in conjunction with metal staples, for purposes of exemplifying preferred embodiments. The fastener applying apparatus can be any of the types which were discussed above.

The resilient film comprises a sheet of resilient polymeric material. The material is preferably bioabsorbable and may be fabricated from polymers of glycolide, lactide, p-dioxanone, caprolactone, trimethylene carbonate, and physical and chemical combinations thereof. The polymeric film may also include effective amounts of therapeutic substances such as antibiotics, growth factors, and other bioactive agents. Such therapeutic substances are disclosed, for example, in U.S. Pat. No. 5,133,738, which is herein incorporated by reference. The film may be of any dimensions suitable for the purposes described herein. Generally, the film thickness may range from 0.001 to about 0.015 inches. More preferably, the film thickness ranges from about 0.008 to 0.012 inches. The length and width are chosen in accordance with the dimensions of the fastener applying apparatus.

Figure 1:
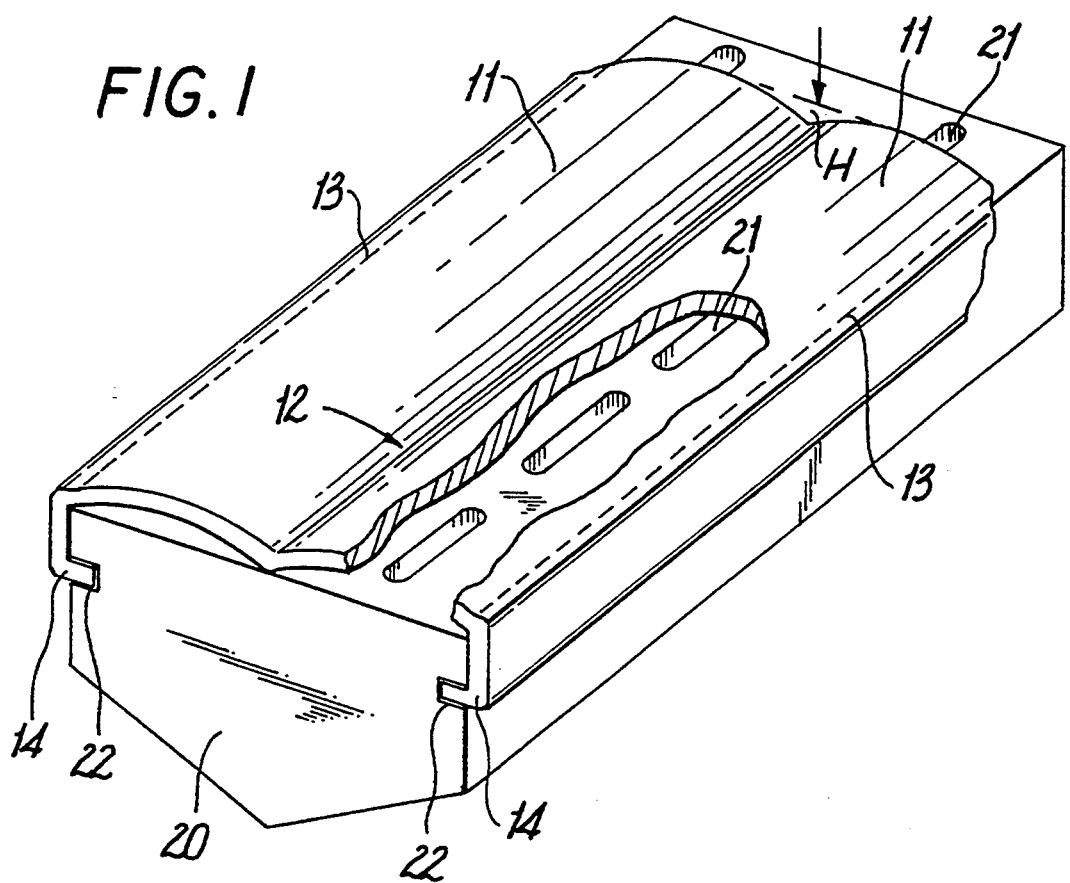
FIG. 1 is a perspective view of an anvil with a curved resilient sheet attached thereto.

Referring now to FIG. 1, a resilient film 10 is shown in conjunction with an anvil 20 of a surgical fastener applying apparatus such as those which simultaneously apply the fasteners to body tissue, as shown in U.S. Pat. Nos. 5,116,349; 4,881,544; 4,881,545; 5,100,042; 4,508,253; 4,522,327; 4,568,009; 4,573,622; 4,665,916; 4,728,020; 4,354,628; 4,383,634; and 3,494,533. Generally, such apparatus apply rows of staples on each side of an incision made by the apparatus. Alternatively, the apparatus may apply rows of staples without creating an incision.

The resilient film 10 has one or more upraised apexes or ridges 11 extending along the film 10 in orientation with the lengthwise extension of the anvil 20. Ridges 11 are separated by a trough or synclinal portion 12 also extending along the length of the anvil. The difference in height H between the top of ridges 11 and the trough 12 may be from about 0.002 inches to about 0.030 inches. The resilient film 10 includes inward pointing elongated projections 14 which are adapted to fit into corresponding slots 22 of the anvil. Optionally, the elongated projections can 14 be securely fixed within slots 22 by means of adhesive bonding with a biocompatible adhesive such as cyanoacrylate. The upraised ridges 11 extend over the lines of staple closing depressions 21 of the anvil 20. A line of perforations 13 extends lengthwise along each side of the film 10 in the vicinity of the side edges. The perforations 13 are adapted to permit tearing of the resilient film 10 along the perforation lines 13 to separate the central portion of the film 10 from the side portions.

In use, the body tissue to be operated upon is clamped between the jaws of the fastener applying instrument and is biased by the resilient film to one or the other of the jaws. The resilient film acts like a spring and permits the instrument jaws to accommodate a wider variation of tissue thicknesses than would an apparatus without such a film 10. A thin piece of tissue will be held by the biasing force of the resilient film 10, whereas the ridges of resilient film 10 will "give" or bend to accommodate a thick piece of tissue. Thus, the resilient film 10 permits a single size fastener applying apparatus to be used in conditions wherein two or more different size apparatus were formerly required.

Figure 2:
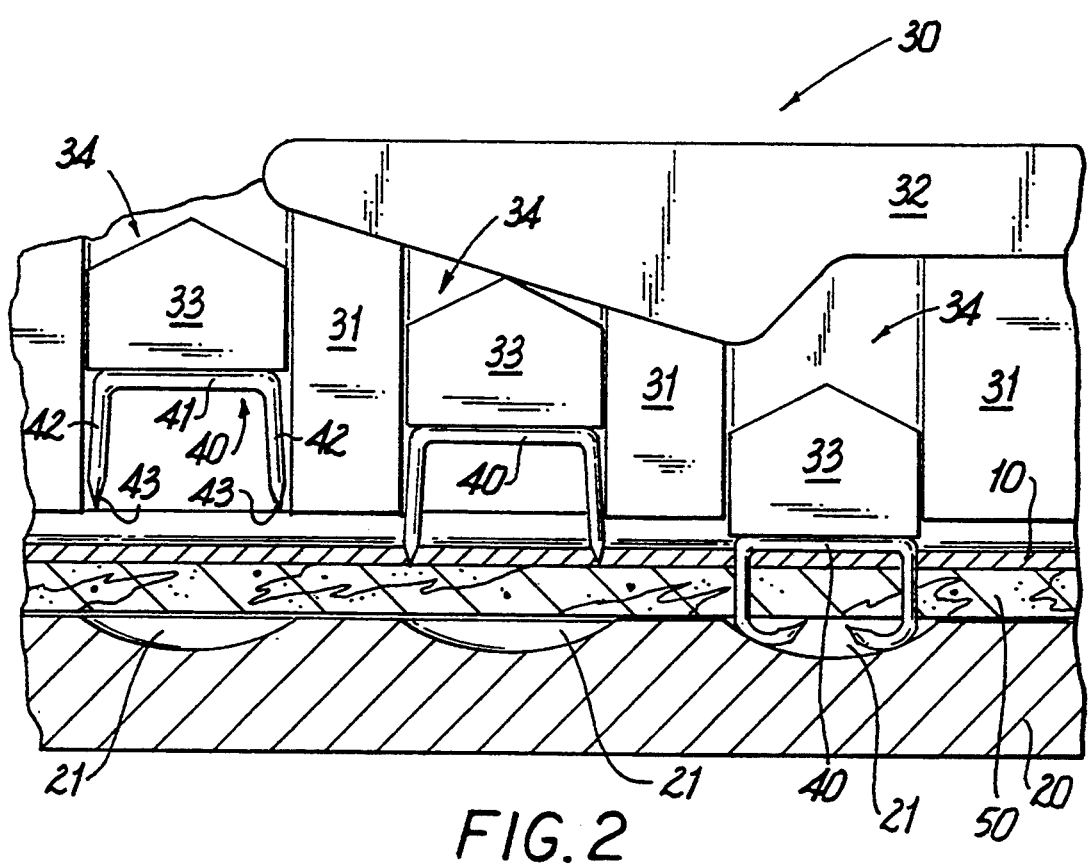
FIG. 2 is a partly sectional elevational view of an apparatus for sequentially applying surgical staples with a resilient sheet attached to the cartridge.

Alternatively, the resilient film 10 may be attached to the fastener holding cartridge of the apparatus. As shown in FIG. 2, the cartridge 30 of a sequentially firing type apparatus, such as shown in U.S. Pat. Nos. 5,156,614; 4,955,959; 5,014,899; 4,520,817; 3,499,591; 3,490,675; and 3,079,606, includes a housing 31 having slots 34 for holding staples 40. A cam bar 32 moves longitudinally through the cartridge 30 when the apparatus is fired, and sequentially contacts and pushes staple drivers 33, which, in turn, push staples 40 out of their respective slots 34 and into staple closing depressions 21 of the anvil 20. The apparatus also includes a longitudinally movable knife blade which cuts the tissue between rows of staples. Thus, the apparatus creates a sealed incision. A resilient film 10 is attached to the cartridge and covers the openings of the staple slots 34. FIG. 2 illustrates a section of the cartridge 30 which has been brought into conjunction with the anvil 20 with body tissue 50 positioned therebetween for stapling. As the cam bar 32 moves distally through the cartridge, i.e. to the left as pictured in FIG. 2, the staples are sequentially driven through the resilient film 10, then through the body tissue 50, and then into staple closing depressions 21 for crimping.

The staples generally comprise a backspan 41 and legs 42 extending from the backspan 41, the legs having sharp points 43 to facilitate tissue penetration. It should be noted that legs 42 have a slight bias outward from each other to facilitate frictional engagement with the walls of the slot 34. This helps retain the staples within the slot. However, this bias has a tendency to cause the legs to undesirably splay a small amount when they are expelled from the slot. Use of the resilient film 10 in conjunction with the cartridge 30 helps to reduce splaying by favoring perpendicular penetration by the legs 42 through the film 10.

Preferably, the resilient film includes apertures 15 for permitting free passage therethrough of the staple legs. Use of an apertured film achieves the benefits and advantages of the resilient film while not significantly increasing the force required to fire the instrument above that of an instrument without resilient film.

Figure 3:
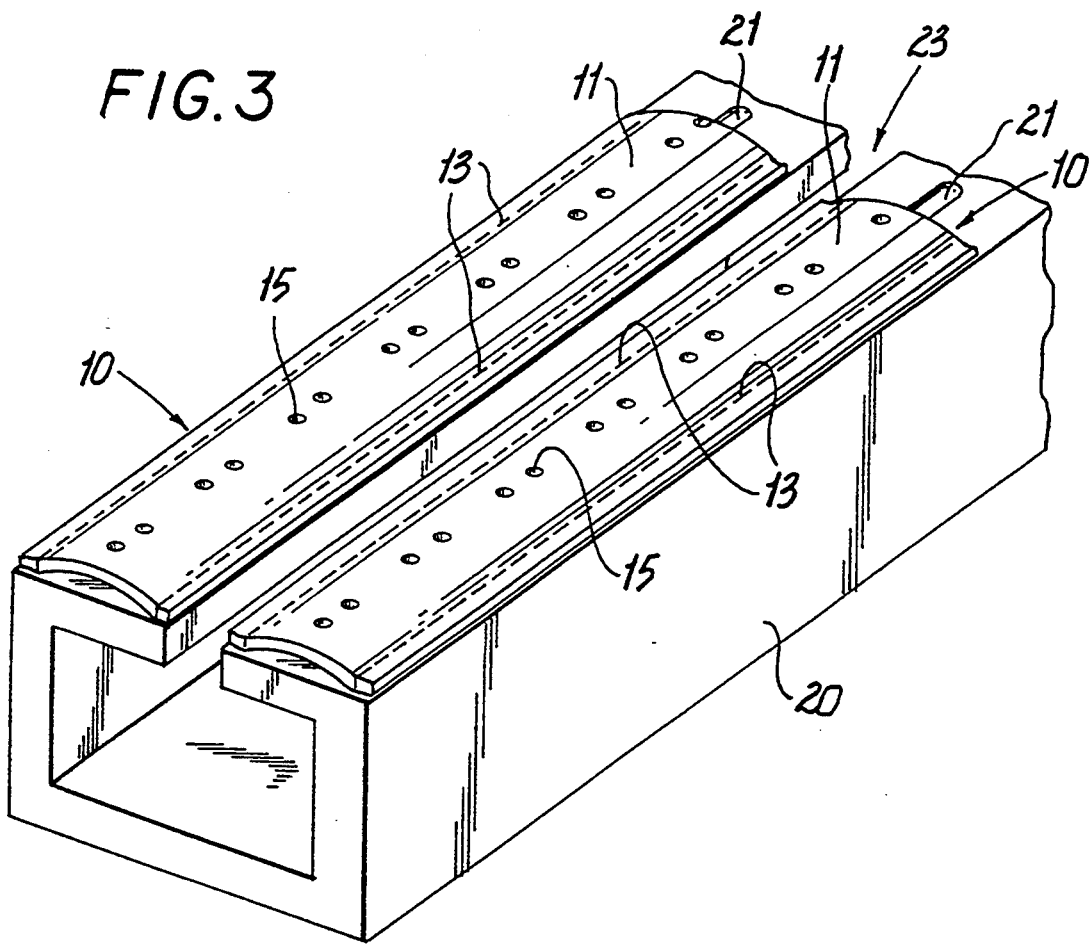
FIG. 3 is a perspective view of an anvil with resilient sheets attached thereto, the anvil including a central knife slot.

In another embodiment shown in FIG. 3, multiple strips of resilient film 10 are positioned on an anvil 20 for an instrument which also cuts body tissue. A knife slot 23 extends through the anvil. The resilient film is preferably attached to the surface of the anvil by adhesive bonding. Perforations 13 permit detachment of the central portion of the resilient film 10 when the stapling operation is completed and the apparatus is opened. After the apparatus is opened the resilient film 10 remains attached to the tissue 50 by means of staples 40.

The resilient film achieves several advantages. First, it helps to distribute the force of the staples over a wider area of body tissue. Second, it achieves greater hemostasis with less oozing of blood or other body fluids at the operation site. Third, it provides a barrier to prevent the operation site from developing surgical adhesions.

A fourth advantage resulting from the use of the resilient film is that it enables a single line of staples to be used on each side of the anvil, as shown in Figs. 1 and 3, instead of the usual two or three rows. Thus, fewer staples may be used while achieving effective hemostasis, thereby reducing the trauma to the tissue and reducing the cost of the apparatus.

Figure 4:
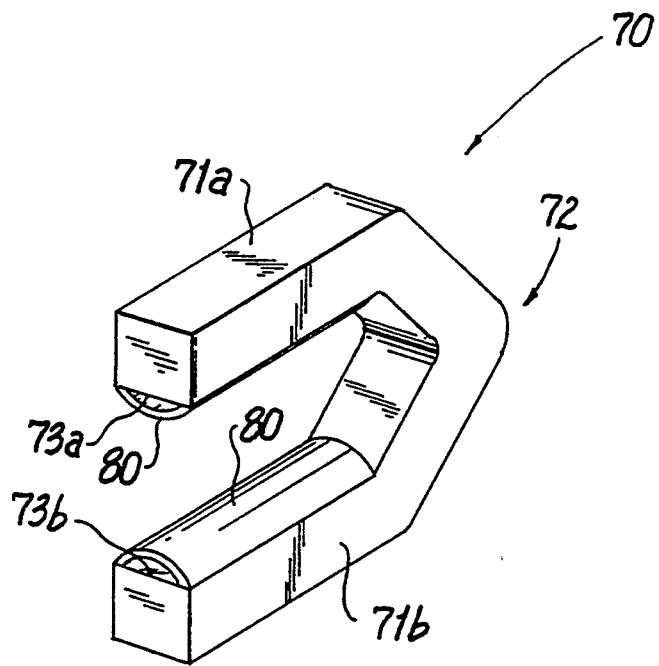
FIG. 4 is a perspective view of a surgical clip having resilient curved sheets attached to the interior of the legs.

FIG. 4 illustrates the use of a resilient sheet 80 in conjunction with the legs of a clip 70. Clip 70 includes parallel legs 71a and 71b joined by a V-shaped or U-shaped bail portion 72. The resilient sheet 80 is affixed to one or both of the inner, mutually facing surfaces 73a and 73b. One skilled in the art recognizes that the inwardly directed convex curvature of the sheet 80 will impart a biasing force to tissue on which clip 70 is applied. Resilient sheet 80 is capable of resilient bending to allow the clip 70 to accommodate a wider range of tissue thickness while maintaining contact with the body tissue.

Clip 70 may be fabricated from stainless steel, titanium, or any other biocompatible metal or plastic with sufficient strength and ductility to bend without breaking. Also suitable are bioabsorbable polymers such as those mentioned above.

The resilient sheet 80 and clip 70 may be integrally fabricated. If, for example, the clip 70 and resilient sheet 80 are both polymeric materials of the same composition clip 70 and resilient sheet 80 may be integrally fabricated by injection molding. Otherwise, resilient sheet 80 may be affixed to clip 70 by adhesive bonding.

While the above description contains many specifics, these specifics should not be construed as limitations on the invention, but merely as preferred embodiments thereof. Those skilled in the art will envision other variations that are within the scope and spirit of the invention as defined by the claims appended hereto.

What is claimed is:

1. A surgical device, which comprises:
   a) first and second elongated members movable between an open first position wherein said members are relatively spaced apart from each other and a closed second position wherein said members are relatively close to each other for clamping body tissue therebetween, said members having mutually facing surfaces;
   b) at least one sheet of resilient material attached to and covering at least a portion of said mutually facing surface of at least one of said members, said sheet of resilient material having a curved surface.

2. The surgical device of claim 1 wherein said surgical device comprises a surgical clip and said first and second elongated members comprise clip legs.

3. The surgical device of claim 2 wherein said clip is fabricated from a material selected from the group consisting of stainless steel, and titanium.

4. The surgical device of claim 2 wherein said surgical clip and said resilient sheet are fabricated from bioabsorbable synthetic polymer.

5. The surgical device of claim 4 wherein said surgical clip and said resilient sheet are integrally fabricated.

6. The surgical device of claim 4 wherein said bioabsorbable synthetic polymer comprises a polymer selected from the group consisting of glycolide, lactide, caprolactone, p-dioxanone, and trimethylene carbonate, and physical and chemical combinations thereof.

7. The surgical device of claim 1 wherein said curved surface of said resilient sheet is a convex surface for contacting body tissue clamped between said first and second members.

8. The surgical device of claim 1 wherein said first member comprises a cartridge for holding a plurality of surgical fasteners.

9. The surgical device of claim 8 wherein said second member comprises an anvil for closing said surgical fasteners.

10. An apparatus for applying surgical fasteners to body tissue, which comprises:
    a) a cartridge for holding a plurality of surgical fasteners;
    b) an anvil having means for closure of surgical fasteners;
    c) means for moving said cartridge and said anvil between an open first position wherein said cartridge and said anvil are relatively spaced apart from each other and a closed second position wherein said cartridge and said anvil are relatively close to each other for clamping body tissue therebetween;
    d) means for driving said fasteners from said cartridge into said anvil for closure thereof; and
    e) a sheet of resilient material positioned between said cartridge and said anvil so that substantially all of the fasteners pass at least partially through said sheet of resilient material in response to firing of said apparatus wherein said sheet of resilient material has a curved surface.

11. The apparatus of claim 10 wherein said fasteners have two legs extending from a backspan and said legs penetrate said resilient sheet when said apparatus is fired.

12. The apparatus of claim 10 wherein said fasteners are metallic staples.

13. The apparatus of claim 10 wherein said fasteners are arranged in rows oriented parallel to a longitudinal axis of the apparatus.

14. The apparatus of claim 13 wherein said fastener driving means sequentially drives the fasteners of said rows.

15. The apparatus of claim 10 further including means for mounting said resilient sheet.

16. The apparatus of claim 15 wherein said means for mounting includes a projection and a slot for receiving said projection.

17. The apparatus of claim 16 wherein said means for mounting comprises adhesive.

18. The apparatus of claim 15 wherein said resilient sheet is mounted to said cartridge.

19. The apparatus of claim 15 wherein said resilient sheet is mounted to said anvil.

20. The apparatus of claim 10 wherein said resilient sheet includes perforations for permitting separation of at least a portion of said sheet.

21. The apparatus of claim 10 wherein said curved surface of said resilient sheet is a convex surface for contacting body tissue clamped between said cartridge and anvil.

22. The apparatus of claim 10 wherein said resilient sheet is fabricated from bioabsorbable synthetic polymer.

23. The surgical device of claim 22 wherein said bioabsorbable synthetic polymer comprises a polymer selected from the group consisting of glycolide, lactide, caprolactone, p-dioxanone, and trimethylene carbonate, and physical and chemical combinations thereof.

24. The surgical device of claim 23 wherein said resilient sheet contains an effective amount of at least one therapeutic agent.

* * * * *